(12) United States Patent
Pino et al.

(10) Patent No.: US 9,907,688 B2
(45) Date of Patent: Mar. 6, 2018

(54) CARE UNIT

(71) Applicant: Regents of the University of Minnesota, Minneapolis, MN (US)

(72) Inventors: Felicity Pino, Kansas City, MO (US); Saurav Paul, Minneapolis, MN (US); James Krocak, Minneapolis, MN (US); John E. Ferguson, Minneapolis, MN (US); Nicole Eugenia Pardo Lamos, Humble, TX (US); David Amor, Glenview, IL (US); Ashish Singal, Blaine, MN (US); Greg Ruth, Chanhassen, MN (US); Blaine Schneider, St. Paul, MN (US); Kari Roberts, St. Paul, MN (US)

(73) Assignee: Regents of the University of Minnesota, Minneapolis, MN (US)

(*) Notice: Subject to any disclaimer, the term of this patent is extended or adjusted under 35 U.S.C. 154(b) by 61 days.

(21) Appl. No.: 13/946,038

(22) Filed: Jul. 19, 2013

(65) Prior Publication Data
US 2014/0060546 A1 Mar. 6, 2014

Related U.S. Application Data

(60) Provisional application No. 61/673,611, filed on Jul. 19, 2012.

(51) Int. Cl.
*A61F 5/37* (2006.01)
*A61N 5/06* (2006.01)
(Continued)

(52) U.S. Cl.
CPC .............. *A61F 5/37* (2013.01); *A61B 5/4836* (2013.01); *A61B 5/6887* (2013.01); *A61F 7/08* (2013.01);
(Continued)

(58) Field of Classification Search
CPC .. A61B 5/6887; A61B 5/4836; A61N 5/0621; A61N 5/06; A61F 5/37; A61F 7/08;
(Continued)

(56) References Cited

U.S. PATENT DOCUMENTS 4,078,560 A * 3/1978 Hill ..................... A61F 5/373
128/881
4,597,121 A * 7/1986 Bouma ................. A41B 13/06
2/69
(Continued)

OTHER PUBLICATIONS

"Commentary: Neonatal Jaundice and Kernicterus", *Pediatrics*, 108(3), (2001), 763-765.
(Continued)

*Primary Examiner* — Victoria J Hicks
*Assistant Examiner* — Michelle J Lee
(74) *Attorney, Agent, or Firm* — Schwegman Lundberg & Woessner, P.A.

(57) ABSTRACT

A care unit can include a base member and a plurality of petal members. Each petal member can extend from a first end, engaged with the base member, to a second end, spaced from the base member. Inward-facing surfaces of at least two petal members and the base member can collectively define a cavity for receiving at least a portion of the patient. The care unit can further include one or both of a therapy component, configured to provide a treatment to the patient, or a sensor component, configured to monitor a condition of the patient. The therapy component can be coupled to, or integrated with, one or both of the base member or a petal member and can include an optical light source, a thermal energy source, an oxygen or air source, a sound wave source, a sound wave-cancelling source, or a pulsating source, for example.

23 Claims, 7 Drawing Sheets

(51) Int. Cl.

| | |
|---|---|
| *A61B 5/00* | (2006.01) |
| *A61M 21/02* | (2006.01) |
| *A61G 7/05* | (2006.01) |
| *A61M 16/00* | (2006.01) |
| *A61F 7/08* | (2006.01) |
| *A61M 21/00* | (2006.01) |
| *A61G 11/00* | (2006.01) |
| *A61G 7/057* | (2006.01) |
| *A61F 7/00* | (2006.01) |

(52) U.S. Cl.
CPC ....... *A61G 7/0526* (2013.01); *A61M 16/0057* (2013.01); *A61M 21/02* (2013.01); *A61N 5/06* (2013.01); *A61N 5/0621* (2013.01); *A61B 5/683* (2013.01); *A61B 5/6892* (2013.01); *A61B 2503/045* (2013.01); *A61B 2560/0412* (2013.01); *A61B 2562/06* (2013.01); *A61F 2007/006* (2013.01); *A61G 7/057* (2013.01); *A61G 11/00* (2013.01); *A61G 2200/14* (2013.01); *A61G 2200/322* (2013.01); *A61G 2200/325* (2013.01); *A61G 2200/327* (2013.01); *A61G 2203/34* (2013.01); *A61G 2203/46* (2013.01); *A61G 2210/70* (2013.01); *A61G 2210/90* (2013.01); *A61M 2021/0022* (2013.01); *A61M 2021/0027* (2013.01); *A61M 2021/0044* (2013.01); *A61M 2021/0061* (2013.01); *A61M 2021/0066* (2013.01); *A61M 2240/00* (2013.01)

(58) Field of Classification Search
CPC ... A61F 5/3776; A61F 5/3784; A61G 7/0526; A61G 13/12–13/1295; A61M 16/0057; A61M 21/02; A41B 13/06; A41B 13/065; A47D 9/00–9/04; A47D 15/005; A47D 15/008
USPC .......................................................... 5/655
See application file for complete search history.

(56) References Cited

U.S. PATENT DOCUMENTS

| | | | |
|---|---|---|---|
| 6,290,713 B1 | 9/2001 | Russell | |
| 6,443,978 B1* | 9/2002 | Zharov | A61N 5/0616 606/13 |
| 6,596,016 B1 | 7/2003 | Vreman et al. | |
| 6,872,220 B2 | 3/2005 | Williams et al. | |
| 9,332,791 B1* | 5/2016 | Bush | A41D 11/00 |
| 2002/0108176 A1* | 8/2002 | Ragen | A47D 13/08 5/482 |
| 2004/0143307 A1* | 7/2004 | Williams | A61N 5/0621 607/88 |
| 2007/0049842 A1* | 3/2007 | Hill | A61B 5/08 600/534 |
| 2007/0179421 A1* | 8/2007 | Farrow | A61H 9/005 602/75 |
| 2010/0263122 A1* | 10/2010 | Papen | A47D 15/003 5/502 |
| 2010/0275373 A1* | 11/2010 | Kaplan | A47D 15/008 5/494 |
| 2011/0231993 A1* | 9/2011 | Schmid | A41B 13/06 5/494 |

OTHER PUBLICATIONS

"Jaundice", [online]. © 2013 Advameg, Inc. [retrieved on Jul. 16, 2013]. Retrieved from the Internet: <URL: http://www.healthofchildren.com/I-K/Jaundice.html>, (2013), 12 pgs.

"Should a mother continue breastfeeding if her child has jaundice?". [online]. Centers for Disease Control and Prevention. [retrieved on Jul. 16, 2013]. Retrieved from the Internet: <URL: http://www.cdc.gov/breastfeeding/disease/jaundice.htm>, (Oct. 20, 2009), 2 pgs.
Atkinson, L. R., et al., "Phototherapy Use in Jaundiced Newborns in a Large Managed Care Organization: Do Clinicians Adhere to the Guideline?", *Pediatrics*, 111, (2003), e555-e561.
Aucott, S., et al., "Neurodevelopmental care in the NICU", *Mental Retardation and Developmental Disabilities*, 8(4), (2002), 298-308.
Conrad, A. L., et al., "Biological and Environmental Predictors of Behavioral Sequelae in Children Born Preterm", *Pediatrics*:125(1), (2010), e83-e89.
De Groote, I., et al., "Extremely Preterm Infants in Belgium (EPIBEL) Study Group. Outcome at 3 years of age in a population-based cohort of extremely preterm infants", *Obstet. Gynecol.*, 110(4), (2007), 855.
De Groote, I., et al., "Outcome at 3 Years of Age in a Population-Based Cohort of Extremely Preterm Infants", *Obstetrics & Gynecology*, 110(4), (2007), 855-864.
Ennever, J. F., et al., "Rapid Clearance of a Structural Isomer of Bilirubin During Phototherapy", *J Clin Invest.*, 79(6), (1987), 1674-1678.
Garg, A. K., et al., "A Controlled Trial of High-Intensity Double-Surface Phototherapy on a Fluid Bed Versus Conventional Phototherapy in Neonatal Jaundice", *Pediatrics*, 95(6), (1995), 914-916.
Gatts, J. D, et al., "A modified newborn intensive care unit environment may shorten hospital stay", *J Perinatal.*. 14(5), (1994), 422-7.
Hack, M., et al., "Behavioral Outcomes and Evidence of Psychopathology Among Very Low Birth Weight Infants at Age 20 Years", *Pediatrics*, 114(4), (2004), 932-940.
Hack, M., et al., "Young Adult Attainments of Preterm Infants", *JAMA*, 295(6), (2006), 695-696.
Hille, E. T., et al., "Social Lifestyle, Risk-taking Behavior, and Psychopathology in Young Adults Born Very Preterm or with a Very Low Birthweight", *J. Pediatr.*, 152(6), (2008), 793-800.
Johnson, S., et al., "Neurodevelopmental Disability Through 11 Years of Age in Children Born Before 26 Weeks of Gestation", *Pediatrics*, 124(2), (2009), e249-e257.
Kramer, L. I., et al., "Rocking waterbeds and auditory stimuli to enhance growth of preterm infants. Preliminary report", *Journal of Pediatrics*, 88, (1976), 297-299.
Lindstrom, K., et al., "Preterm Birth and Attention-Deficit/Hyperactivity Disorder in Schoolchildren", *Pediatrics*:127(5), (2011), 858-865.
Marlow, N., "Neurologic and developmental disability at six years of age after extremely preterm birth", *N. Engl. J. Med.*, 352(1), (2005), 9-19.
Mikkola, K., et al., "Neurodevelopmental Outcome at 5 Years of Age of a National Cohort of Extremely Low Birth Weight Infants Who Were Born in 1996-1997", *Pediatrics*,116(6), (2005), 1391-1400.
Morris, B. H., et al., "Aggressive vs. Conservative Phototherapy for Infants with Extremely Low Birth Weight", *N. Engl. J. Med.*, 359, (2008), 1885-1896.
Neu, M., et al., "Infant physiologic and behavioral organization during swaddled versus unswaddled weighing", *J. Perinatol.*, 17(3), (1997), 193-198.
Oehler, J. M., et al., "Developmental Care of the Low Birth Weight Infants", *Nursing Clinics of North America*, 28(2), (1993), 289-301.
Short, M. A., et al., "A comparison of temperature in VLBW infants swaddled versus unswaddled in a double-walled incubator in skin control mode", *Neonatal Network*, 7(3), (1998), 25-31.
Short, M. A., et al., "The Effects of Swaddling Versus Standard Positioning on Neuromuscular Development in Very Low Birth Weight Infants", *Neonatal Network*, 15(4), (1996), 25-31.
Wood, N. S., et al., "Neurologic and developmental disability after extremely preterm birth. EPICure Study Group", *N. Engl. J. Med.*, 343(6), (2000), 378-384.

\* cited by examiner

CARE UNIT

CLAIM OF PRIORITY

This patent matter claims the benefit of priority under 35 U.S.C. § 119(e) to U.S. Provisional Patent Application Ser. No. 61/673,611, entitled "NEONATAL CARE UNIT," filed on Jul. 19, 2012, which is hereby incorporated by reference in its entirety.

TECHNICAL FIELD

This patent matter pertains to care units and related methods.

BACKGROUND

Each year, 13 million neonates are born prematurely (i.e., less than 37 weeks gestational age) worldwide. This number is growing due to medical and healthcare advances allowing premature neonates to survive and develop outside an in vivo uterine environment.

Premature neonates are at higher risk than neonates born full-term for neurodevelopmental disability at school age and adolescence. Premature neonates are also at higher risk of experiencing medical and social disabilities in adulthood. These risks are inversely related to gestational age and weight at birth. For neonates born extremely premature, impaired cognition and motor/neurosensory deficits occur frequently, can be severe, and can persist into school age and young adulthood.

Studies have shown that premature neonates can benefit from placement in a uterine-similar environment to optimize development (e.g., neurological or neuromuscular development), especially prior to reaching 37 weeks gestational age. Uterine simulation is associated with increased growth rates and reduced hospital stays.

Other studies have shown that all neonates, both premature and full-term babies, can benefit from proper post-birth positioning while neuromuscular mechanisms are in development. Proper positioning can result in neuromuscular benefits, including reduced crawling and walking delays, more efficient energy and oxygen expenditure, and increased core temperature.

In addition to a uterine-similar environment and proper post-birth positioning, another need for neonates is the treatment of hyperbilirubinemia. Bilirubin is a by-product of red blood cell replacement, which is a normal process within a healthy, functioning body. Bilirubin is converted to an excretable form by a properly functioning liver. If a liver hasn't yet matured fully or if red blood cell replacement is occurring at an excessive rate, excess bilirubin accumulates in the body. If bilirubin accumulation is sufficiently elevated, the neonate can become lethargic and hypotonic, which, without treatment, can cause hypertonia or fever. Hyperbilirubinemia can eventually result in cerebral palsy, hearing loss, dental dysplasia, gaze paralysis, or permanent intellectual or neurodevelopmental handicaps. Excess bilirubin results in a jaundiced, or yellowed, pigmentation of skin and mucosal membranes and, as such, this condition is commonly referred to as "jaundice." It is estimated that mild jaundice occurs in approximately 60% of full-term neonates and approximately 80% of premature neonates. Severe jaundice is estimated to occur in approximately 7% of full-term neonates and approximately 50% of premature neonates.

OVERVIEW

The present inventors recognize, among other things, that current approaches of treating select patient conditions are inadequate. The present care units satisfy outstanding needs by providing a comfortable environment for a patient, such as term and preterm neonates or newborns, that can simulate one or more features of a uterine environment, expedite or assist patient development, reduce a patient's hospital stay, stress level, crying and severity of infections, and provide visual comfort to caregivers and parents unable to hold the patient. The care units can maintain a desired patient positioning relative to a support surface on which the unit is placed to facilitate neuromuscular development. The present care units can provide optical, thermal or other therapy in close proximity to a patient's skin (e.g., to benefit those that are jaundiced or hyperbilirubinemic), while restricting select patient movements and allowing for desired caregiver or equipment access to the patient.

To illustrate the care units and related methods disclosed herein, a non-limiting list of examples is provided below.

In Example 1, a care unit can include a base member and a plurality of petal members. The plurality of petal members can optionally be disposed around at least half of a perimeter of the base member. Each petal member can extend from a first end, engaged with the base member, to a second end, spaced from the base member, and have an inward-facing surface and an outward-facing surface. The inward-facing surfaces of at least two or at least three petal members in conjunction with the base member can define a cavity for receiving at least a portion of a patient (e.g., a neonate or a newborn under 15 pounds).

In Example 2, the care unit of Example 1 is optionally configured such that one or more of the plurality of petal members has a rigidity sufficient to maintain a shape of the cavity.

In Example 3, the care unit of Example 2 is optionally configured such that the one or more petal members include a metallic structure.

In Example 4, the care unit of any one or any combination of Examples 1-3 is optionally configured such that the first ends of the plurality of petal members are coupled to the perimeter of the base member.

In Example 5, the care unit of any one or any combination of Examples 1-4 is optionally configured such that the base member defines a void configured to receive a flowable material to support the patient in a desired orientation.

In Example 6, the care unit of any one or any combination of Examples 1-5 is optionally configured such that a size or a shape of the base member is adjustable.

In Example 7, the care unit of any one or any combination of Examples 1-6 is optionally configured such that the base member includes an adjustment mechanism configured to maintain a selected angular alignment or a selected elevation between a plane of the base member and an underlying support surface on which the base member rests.

In Example 8, the care unit of any one or any combination of Examples 1-7 optionally further comprises a therapy component configured to provide a treatment to the patient. The therapy component can be coupled to, or integrated with, one or both of the base member or a petal member.

In Example 9, the care unit of Example 8 is optionally configured such that the therapy component includes one or more of an optical light source, a thermal energy source, an oxygen or air source, a sound wave source, a sound wave-cancelling source, or a pulsating source.

In Example 10, the care unit of any one or any combination of Examples 1-9 is optionally configured such that at least one of the plurality of petal members includes an attached or integral fastener member. The fastener member can be configured such that, when in a loosened or detached configuration, it permits the petal member to change in shape or position and, when in a tightened or attached configuration, it inhibits the petal member from changing shape or position.

In Example 11, the care unit of Example 10 is optionally configured such that the fastener member includes a cable.

In Example 12, the care unit of Example 10 is optionally configured such that the fastener member includes hook and loop fastener portions near the second end of the at least one petal member.

In Example 13, the care unit of any one or any combination of Examples 1-12 is optionally configured such that the outward-facing surfaces of the plurality of petal member have a hardness greater than the inward-facing surfaces. Optionally, the outward-facing surface of at least one petal member can include indicia providing an indication of an enveloped patient or company advertising (e.g., for funding purposes).

In Example 14, the care unit of any one or any combination of Examples 1-13 optionally further comprises a sensor coupled to, or integrated with, one or both of the base member or a petal member for sensing or monitoring a condition of the patient.

In Example 15, a method comprises placing a patient (e.g., a neonate or newborn under 15 pounds) on a base member surrounded, at least in part, by a plurality of petal members and enveloping the patient. Each of the petal members have a first end engaged with the base member and have a second end disposed longitudinally away from the base member. Enveloping the patient can include wrapping the plurality of petal members about a portion of the patient and less than 360 degrees relative to respective petal member first ends.

In Example 16, the method of Example 15 optionally further comprises providing therapy to the patient.

In Example 17, the method of Example 16 is optionally configured such that providing therapy to the patient includes directing an optical light or a thermal energy wave toward a portion of the patient.

In Example 18, the method of any one or any combination of Examples 15-17 is optionally configured such that placing the patient on the base member includes placing the patient on a circular, oval, or octagonal base member surrounded by the plurality of petal members around at least half of the base member's perimeter.

In Example 19, the method of any one or any combination of Examples 15-18 is optionally configured such that wrapping the plurality of petal members about the portion of the patient includes introducing a bend into one or more of the petal members, thereby bringing the second ends of the petal members closer to the patient.

In Example 20, the method of any one or any combination of Examples 15-19 is optionally configured such that wrapping the plurality of petal members about the portion of the patient includes providing support to the patient's arms, hands, legs, feet, abdomen, and chest region.

In Example 21, the method of any one or any combination of Examples 15-20 is optionally configured such that wrapping the plurality of petal members about the portion of the patient includes creating a customized cavity that supports the patient and allows for proper ventilation.

In Example 22, the method of any one or any combination of Examples 15-21 optionally further comprises maintaining a longitudinally extension of at least one petal member away from the base member to provide support to the patient's head.

In Example 23, the method of any one or any combination of Examples 15-22 optionally further comprises disengaging one or more petal members from the base member.

In Example 24, the care unit or method of any one or any combination of Examples 1-23 can optionally be configured such that all elements, operations, or other options recited are available to use or select from.

These and other examples and features of the present care units and related methods will be set forth, at least in part, in the following Detailed Description. This Overview is intended to provide non-limiting examples of the present subject matter—it is not intended to provide an exclusive or exhaustive explanation. The Detailed Description below is included to provide further information about the present care units and related methods.

BRIEF DESCRIPTION OF THE DRAWINGS

In the drawings, like numerals can be used to describe similar elements throughout the several views. Like numerals can be used to represent different views or configurations of similar elements. For example, elements of the neonatal care units having the same last two numerals may correspond to similar, but not necessarily identical, structures. The drawings illustrate generally, by way of example, but not by way of limitation, various embodiments discussed in the present document.

DETAILED DESCRIPTION

The present care units, primarily discussed herein as neonatal care units, can provide a comfortable environment defining proper developmental positioning for a patient, primarily discussed herein as a neonate, in conjunction with optical, thermal or other therapy. The environment can expedite or assist neonatal development, reduce a neonate's hospital stay, stress level, crying and severity of infections, and provide visual comfort to caregivers and parents unable to hold the neonate. The therapy can be applied in close proximity to the neonate, potentially enhancing and expediting the effect of the therapy. Optionally, the care units can be used for patients other than neonates, such as for geriatrics, pediatrics, adult care, and pet care applications.

Figure 1:
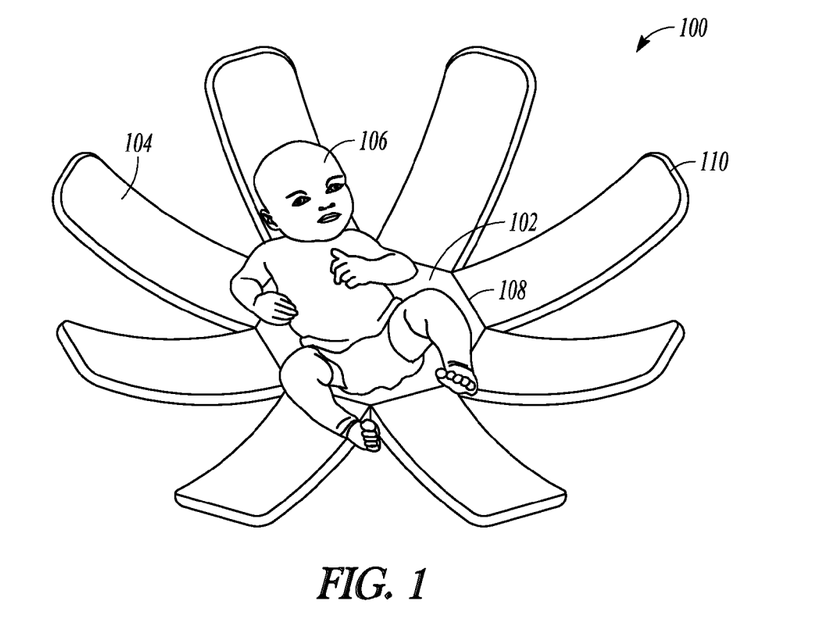
FIG. 1 illustrates a care unit (e.g., a neonatal care unit), as constructed in accordance with at least one embodiment, and a doll, representing a patient. The care unit includes a plurality of petal members in an open position, wherein second, outer ends of the petal members are positioned away from a base member and the doll.

FIG. 1 illustrates a neonatal care unit 100, including a base member 102 and a plurality of petal members 104, and a doll 106, representing a neonate. The plurality of petal members 104 can be disposed around at least half of a perimeter of the base member 102, with each petal member 104 extending from a first end 108, engaged with the base member 102, to a second end 110, spaced from the base member 102. In the example shown, the petal members 104 are disposed 360 degrees around the base member 102. In some examples, a first petal member 104 is disposed on a first side of the base member 102 and a second petal member 104 is disposed on a second, different side of the base member 102.

Figure 2:
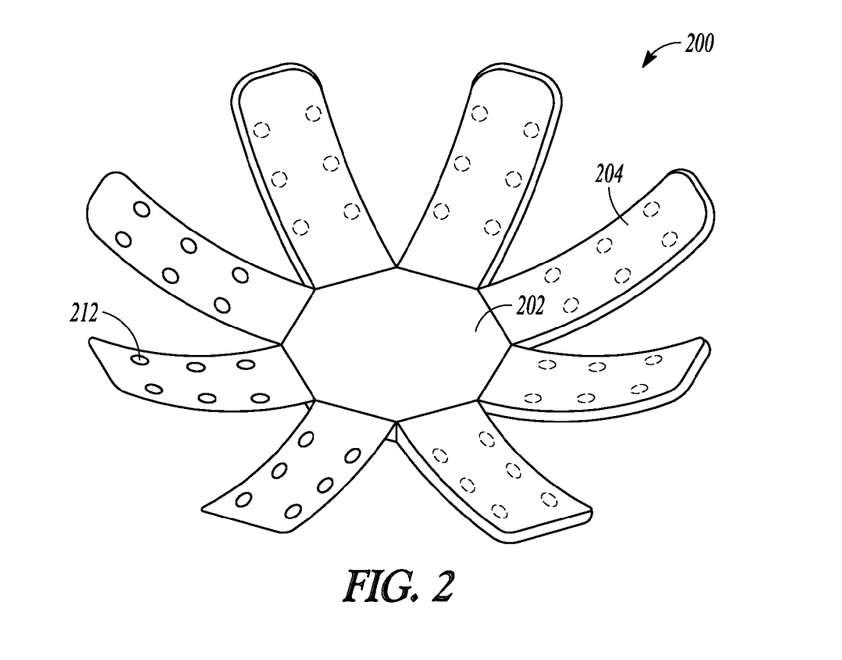
FIGS. 2 and 3 illustrate partially exposed care units including a therapy component, as constructed in accordance with at least one embodiment.

The base member 102 can be configured in various or adjustable shapes, sizes, and weights. For example, the base member 102 can be octagonal, as illustrated in FIGS. 1 and 2, oblong, circular, or other shapes that closely fit a neonate's body outline. The base member 102 can be configured to sustain a compressive load, such as load associated with emergency CPR, and can have a weight that balances a collective weight of the plurality of petal members 104 and the neonate 106. In an example, the base member 102 can be composed of a polymer structure, such as a compressible polymer structure, or a metal structure.

Optionally, the base member 102 can include an adjustment mechanism configured to maintain a selected angular alignment or a selected elevation between a plane of the base member 102 and an underlying support surface on which the base member 102 rests. In an example, the adjustment mechanism can include a void defined by the base member 102. The void can be configured to receive a flowable material to support the neonate 106 in a particular orientation, relative to the underlying support surface, to facilitate one or more aspects of the neonate's development. In an example, the adjustment mechanism can be configured to orient the neonate in an inclined position relative to the support surface to facilitate the neonate's gastro-esophageal development. In an example, the adjustment mechanism can be configured to orient the neonate in a prone position, with the neonate's limbs resting downward in order to facilitate the neonate's neuromuscular development and reduce pressure on the limb joints (e.g., knees and elbows). The adjustment mechanism can include a component placed below and optionally coupled to the base member 102.

The plurality of petal members 104 can be configured in various or adjustable shapes, sizes, and weights appropriate for supporting the neonate's 106 head or feet or creating a cavity above the neonate's abdomen and chest region. Additionally, each petal member 104 can have multiple degrees of freedom, relative to the base member 102, to define a user-desired cavity in conjunction with the base member 102. Each petal member 104 can include one or more hinged extensions that can be folded inward (i.e., toward the base member 102 or neonate 106) to create an overhead cover for the neonate, such as for shielding the neonate from light or other environmental elements. At least one petal member 104 can be disengaged from the base member 102 when the neonate is placed in a prone or supine position. Disengagement of the at least one petal member 104 can include unhinging, unsnapping, or unhooking a petal member 104 from the base member 102, for example. Quick release fasteners brought into coupling engagement or disengagement via a rotational, sliding, or push-button movement can also be used to couple and decouple the at least one petal member 104 to/from the base member 102. The neonate's limbs can extend through the voids left by the disengaged petal member(s) 104 and rest downward.

The neonatal care unit 100 can provide a one-size-fits-all assembly, in that the petal members 104 can extend a length sufficient to wrap around and enclose neonates of varying shapes, sizes, and rotational positions (e.g., supine, prone, etc.). Since each petal member's position and shape can be independently modified by a caregiver, an overall shape of the neonatal care unit 100 can be based, in part, on a visibility defined by a caregiver or a neonate's position, shape, and size.

Figure 3:
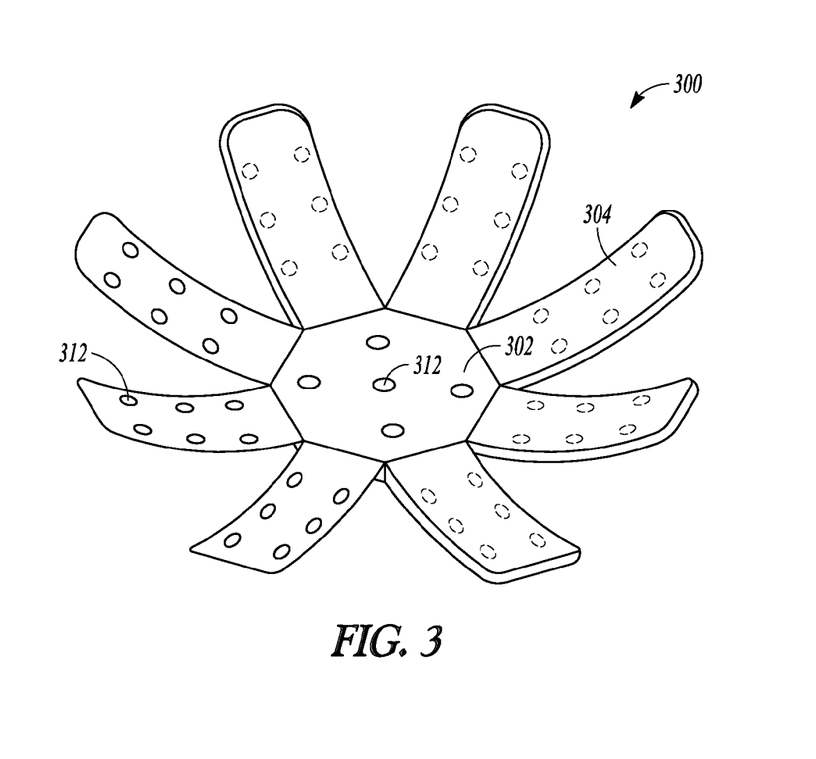

FIGS. 2 and 3 illustrate neonatal care units 200, 300 including a therapy component 212, 312. Alternatively or additionally, the neonatal care units 200, 300 can include a sensor component. The therapy component 212, 312 or the sensor component can be coupled to, or integrated with, at least one of a base member 202, 302 or a petal member 204, 304. Therapy components 212, 312 in certain petal members and the base member 302 are shown exposed. As illustrated in FIG. 2, the therapy component 212 or the sensor component can be integrated in a plurality of petal members 204 and surrounded by a distinct cover, through which the therapy or sensing can be effectuated. As illustrated in FIG. 3, the therapy component 312 or the sensor component can be coupled to a plurality of petal members 304 and can be integrated with a base member 302.

Various therapy 212, 312 and sensor components can be included in the neonatal care units 200, 300. The sensor components can include one or more of a blood monitor, a heart rate monitor, an EKG monitor (e.g., a piezoelectric sensor), a temperature monitor, a respiration rate monitor, a blood pressure monitor, a pulse oximetry monitor, a capnography monitor, a cardiac output monitor, a sound level monitor, a vibration level monitor, a photo-intensity monitor, or a contact-pressure monitor. A plurality of contact-pressure monitors, for example, can be included in the plurality of petal members 204, 304 and/or the base member 202, 302 to create a contoured map of pressure points for an enveloped neonate. Information about the pressure points can be used to adjust a position, size, or shape of one or more petal members 204, 304 automatically, by way of, for example, a feedback loop, or manually. For example, based on the pressure point information, a fluid filling within a petal member or base cavity can be increased or decreased to reduce or eliminate pressure point contact.

Based on a variety of monitored factors, a processor electronically coupled with the sensor components can generate for a particular neonate a distress level calculation, a Sudden Infant Death Syndrome (SIDS) calculation, or an activity level calculation. The monitored sensor values can be electronically recorded in the processor or elsewhere for later clinician use. The neonatal care unit 200, 300 can communicate the monitored sensor values with a central caregiver database, a bed side monitor, or a home personal computer using embedded Bluetooth telemetry. The monitored sensor values can be visually displayed, in real-time, on a monitor attached to an outer or external surface of the neonatal care unit 200, 300. A battery power level can also be visually displayed on the monitor.

The therapy component 312 can include one or more of an optical light source driven by the neonate's sensed blood bilirubin levels, a thermal energy or cooling source driven by the neonate's sensed temperature, or an oxygen or air source driven by the neonate's sensed oxygen levels. The air source can deliver temperature controlled and humidity controlled air to keep the neonate comfortable by constantly circulating fresh air. Each therapy component 312 can be configured with adjustable settings (e.g., intensities, volumes, etc.).

The neonatal care units 200, 300 can include one or more therapy components 212, 312 providing sensory features to comfort and calm a neonate. A programmable pulsating mechanism designed to simulate maternal heart rate motion can be coupled to, or integrated with, at least one of the base member 202, 302 or a petal member 204, 304. An air filter unit can be incorporated with the neonatal care units 200, 300 to filter surrounding air before it is inhaled by the neonate. A rocking motion generator, speakers (e.g., supplying white noise, music or a recorded voice), and/or noise-cancelling equipment can be included to calm the neonate during periods of distress. A microphone can additionally or alternatively be incorporated into the neonatal care units 200, 300 for monitoring purposes. The various therapy 212, 312 and sensor components can be selected from lower power therapy and sensor components and powered by one or more rechargeable batteries stored within the base member or a petal member for easy care unit 200, 300 transport and portability.

Figure 4:
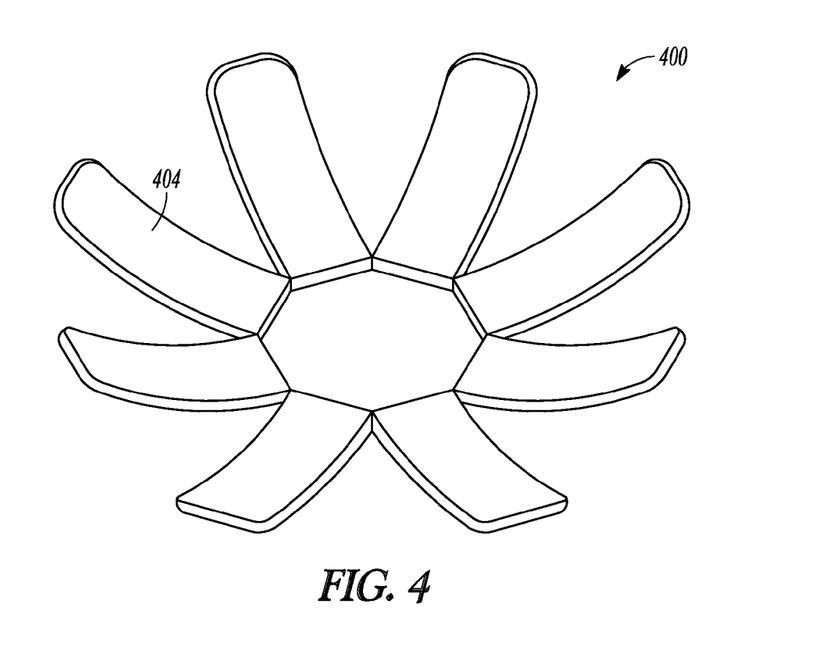
FIGS. 4 and 5 illustrate eight petal members of a care unit, shown without a base member and in an open or semi-open position, as constructed in accordance with at least one embodiment.
Figure 5:
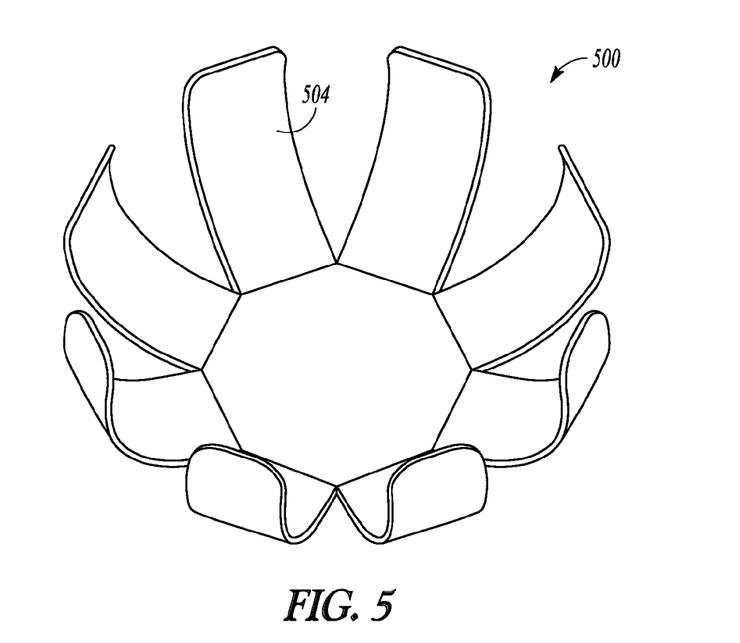

FIGS. 4 and 5 illustrate eight petal members 404, 504 of neonatal care units 400, 500. The eight petal members 404 of FIG. 4 are illustrated in an open position, which allows for receipt of a neonate. The eight petal members 504 of FIG. 5 are illustrated in a semi-open position; a position defined by a caregiver through movement of one or more petal members 504 from an open position toward a base member (not shown) or the neonate. Bending of the one or more petal members 504 brings the petal member second ends closer to the neonate.

Inward-facing surfaces of at least two or at least three petal members 404, 504 and the base member can define a cavity for receiving and supporting at least a portion of the neonate. One or more of the petal members 404, 504 can possess a rigidity sufficient to maintain a shape of the cavity. In an example, one or more of the petal members 404, 504 include a metallic or plastic (e.g., polycarbonate) material. The petals 404, 504 can be malleable for a caregiver to shape as desired, yet stiff enough to retain a supportive shape or position in response to limb forces (e.g., leg kicks) from the neonate. In an example, the petal members can retain the supportive shape or position without the use of a fastener member, as discussed in associated with FIG. 7 below.

Figure 6:
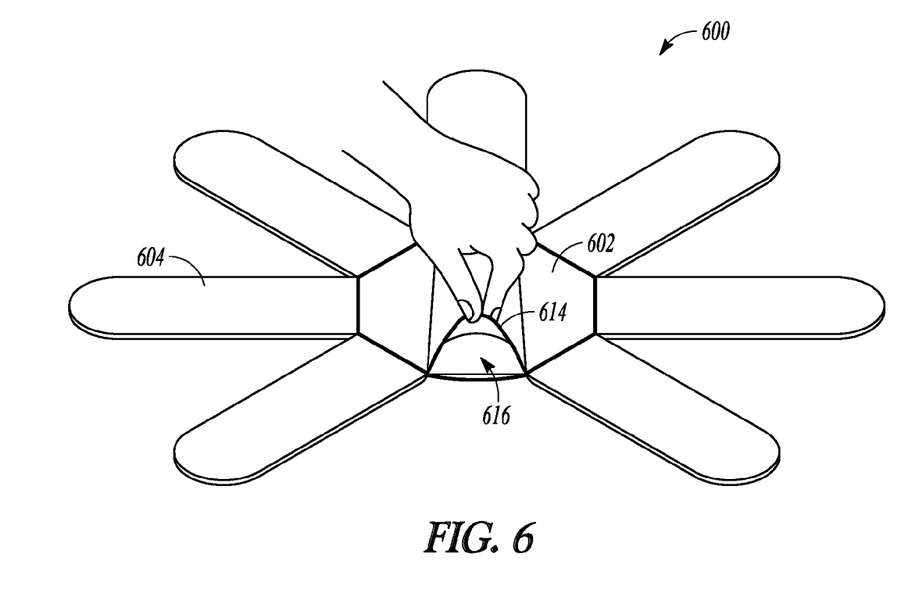
FIG. 6 illustrates a petal member engaged with a perimeter of a base member and including a pocket, as constructed in accordance with at least one embodiment.

FIG. 6 illustrates a neonatal care unit 600 including a plurality of petal members 604 mechanically, and optionally, electrically, engaged with a perimeter of a base member 602. The mechanical engagement can allow each petal member 604 to securely attach to the base member 602 and the electrical engagement can allow therapy or sensor component activation and bi-directional data flow. Mechanical engagement between the petal members 604 and the perimeter of the base member 602 can include a rotating pivot or hinge joint, a snap, hook and loop, tongue and groove, or a weld, for example. The mechanical engagement between the petal members 604 and the perimeter of the base member 602 can also come by way of one or more quick-release connectors, such as ¼-, ½-, or ¾-turn fasteners, cam fasteners, sliding fasteners, or push-button fasteners. Through simple rotational, sliding, or push-button activating movement of the one or more quick-release connectors, for example, the petal members 604 can be quickly removed from, or attached to, the base member 602 for cleaning, repairing, or replacement.

The petal members 604 and the base member 602 can be surrounded by a soft and flexible material 614 (e.g., cotton or polyester) providing comfort to a received neonate. A pocket 616 can be defined between the petal members 604 and the surrounding material 614. The pocket 616 can be filled with, or carry, a filler such as foam, liquid, air or other deformable material, a therapy component, or a sensor component. The surrounding material 614 can be relatively thin or loosely woven or the fabric fibers can be transparent or translucent to permit therapy light, for example, to pass. For a similar reason of permitting the transmission of therapy light, the petal members 604 or the base member 602 can be made from a transparent or translucent material.

Various materials can be used to surround the one or more of the petal members 604. The surrounding material 614 can be hypoallergenic, non-flammable, non-toxic, lightweight, and compatible with phototherapy components or warming lamp radiation components. The surrounding material 614 can be washable, if intended for reuse, or disposable. Surrounding material 614 on an inward facing side of a petal member 604 can be made of a material that is low-risk for SIDS, such as knit cotton, and can have a hardness less than an outer surface of the surrounding material 614. The surrounding material 614 can optionally provide or reflect heat to the received neonate. The surrounding material 614 on the outer surface of a petal member 604 can include a durable, impact resistant material, designed to support the neonatal care unit 600 atop most any surface or within the arms of a caregiver. The surrounding material 614 can be secured to a petal member 604 or the base member 602 by adhesive or a hook and loop fastener, for example. Optionally, the surrounding material 614 can be infused with antimicrobial materials (e.g., silver particles) or a maternal scent.

Since neonates are commonly scanned by x-rays or magnetic resonance imaging following birth, components of, or coupled to, the neonatal care unit 600 including petal members, the base member, and embedded sensor or therapy components can be made compatible with x-rays or magnetic resonance images. As a result, the components should not materially alter the x-ray or magnetic resonance images. Optionally, one or more components (e.g., a phototherapy component) of the neonatal care unit 600 can include a recognized pattern that is distinguishable from the neonate in an x-ray or a magnetic resonance image.

To allow periodic neonatal bathing, the components of the neonatal care unit 600 can be water compatible.

Figure 7:
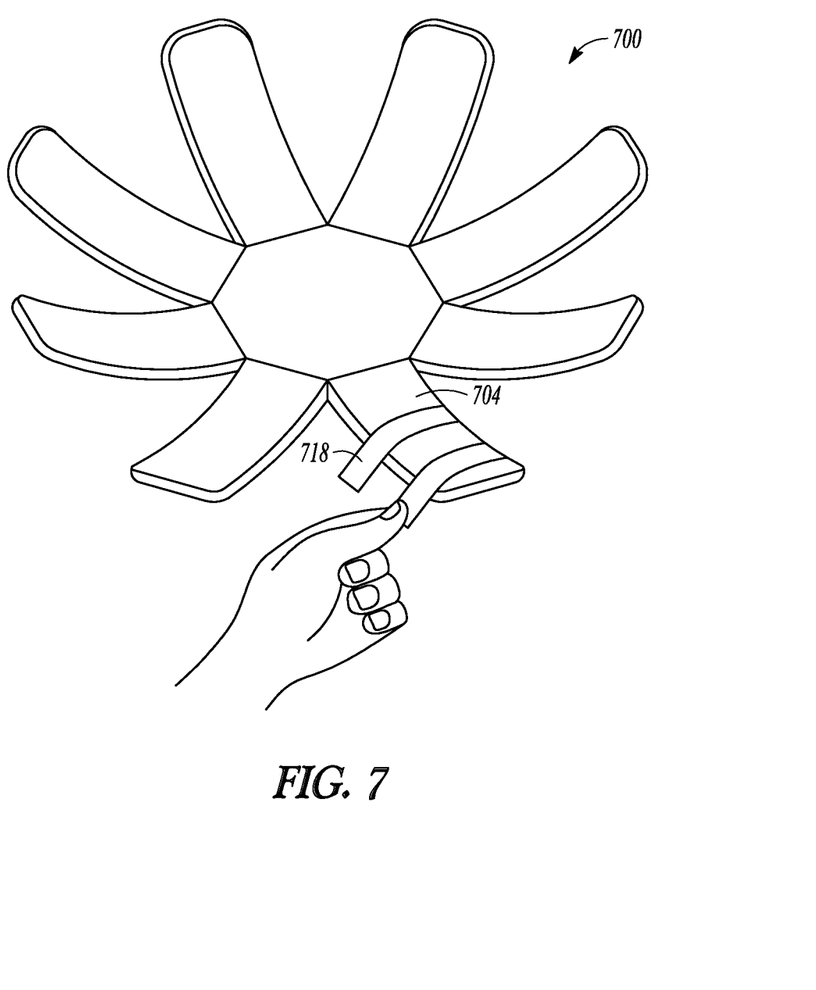
FIG. 7 illustrates a fastener member attached to a petal member, as constructed in accordance with at least one embodiment.

FIG. 7 illustrates a fastener member 718 attached to an outer end a petal member 704 of a neonatal care unit 700. The fastener member 718 can be used to hold adjacent petal members 704 securely to one another and in place around a neonate. The fastener member 718, when in a loosened or detached configuration, can permit one or more petal members 704 to change in shape or position and, when in a tightened or attached configuration, can inhibit the one or more petal members 704 from changing shape or position. In an example, the fastener member 718 includes hook and loop fastener portions, which is also known by its registered trademark, VELCRO. In an example, the fastener member 718 includes a cable.

Figure 8:
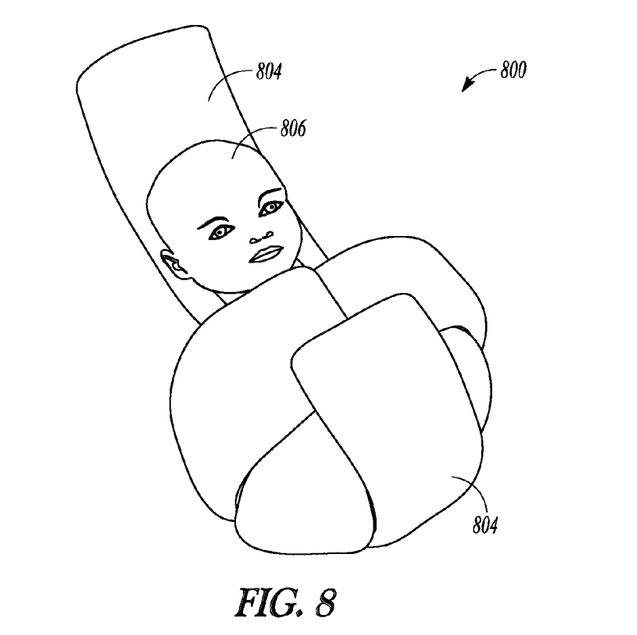
FIG. 8 illustrates a care unit including a plurality of petal members in a closed position around a doll, representing a patient, and one petal member in an open position to receive the head of the patient. In the closed position, second, outer ends of the plurality of petal members are positioned around the doll.
Figure 9:
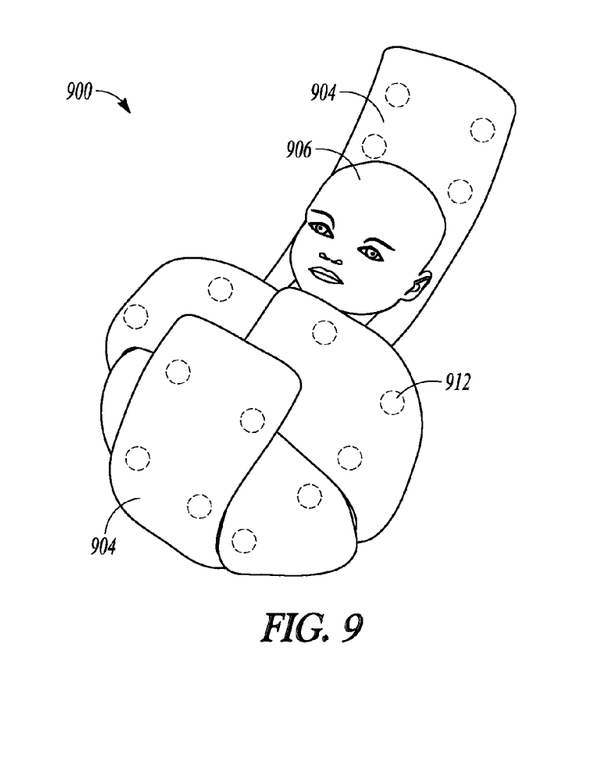
FIG. 9 illustrates a care unit including a plurality of petal members in a closed position around a doll, representing a patient, and providing therapy to the doll.

FIGS. 8 and 9 illustrate neonatal care units 800, 900 including a plurality of petal members 804, 904 in a closed position around a doll 806, 906, representing a neonate, and one petal member 804, 904 in an open position to receive the head of the neonate. As illustrated, the plurality of petal members 804, 904 in the closed position can envelop the neonate and provide close contact to the body surface (i.e., the skin) of the neonate. Advantageously, the neonatal care units 800, 900 do not require lifting or transfer of the neonate to secure a proper or snug supportive fit. Additionally, the neonatal care units 800, 900 can be easily rotated or moved (e.g., to a supine, prone, right or left lateral recumbent direction) on a regular basis to promote proper neonatal lung development, prevention of pressure ulcers, or prevention of head shape deformations.

It is estimated that mild jaundice occurs in approximately 60% of full-term neonates and approximately 80% of premature neonates. Severe jaundice occurs in approximately 7% of full-term neonates and approximately 50% of premature neonates.

Neonates experiencing elevated bilirubin levels can be treated with the use of phototherapy, which is the use of light absorbable through a neonate's skin to convert and facilitate the breakdown of bilirubin. As illustrated in FIG. 9 and discussed elsewhere in this document, a therapy component 912 can be coupled to, or integrated with, one or more of the petal members 904 or a base member to provide therapy in close proximity to the neonate. The therapy component 912 can include a light emitting diode or fiber optics coupled to, or integrated with, one or more petal members 904 or a base member and configured to emit light at an intensity and wavelength suitable for treatment or prevention of hyperbilirubinemia. It is believed that light having a wavelength of 425-475 nanometers and an irradiance of 6-30 microwatts per square centimeter can be absorbed by the neonate and bilirubin converted to less toxic water-soluble photo isomers. Near-skin phototherapy, for example, can be provided from any angle that a caregiver desires using the present neonatal care units, including from above and below the neonate, to create an omni- or near omni-directional field. It is believed that providing near-skin phototherapy overhead and under the neonate can reduce bilirubin levels multiple times faster than using overhead phototherapy alone.

The therapy component 912 can be in communication with one or more pressure sensors embedded into the base member or a petal member 904 for automatic activation of the therapy component 912 upon placement of the neonate within the care unit 900 or wrapping of the petal members 904 around the neonate. The presence of the neonate can be sensed by the one or more pressure sensors and the therapy component (e.g., a light source) can be automatically activated (e.g., illuminated) without a manual on/off switch. Advantageously, automatic therapy activation can encourage energy savings and can reduce unnecessary light or other therapy exposure.

Figure 10:
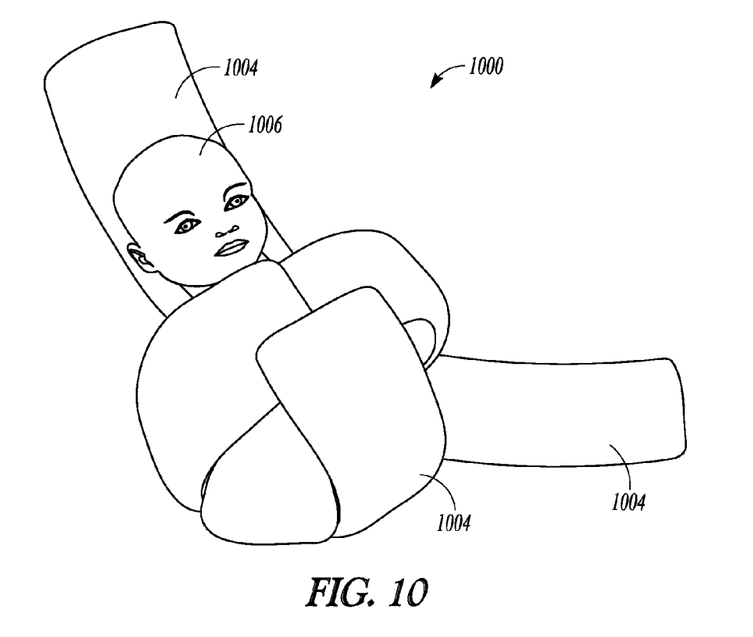
FIG. 10 illustrates a care unit including a plurality of petal members in a closed position around a doll, representing a patient, and two petal members in an open position. One petal member is positioned to receive the head of the patient and another petal member, shown near a left leg of the patient, provides external access for a caregiver or non-integrated equipment.

FIG. 10 illustrates a neonatal care unit 1000 including a plurality of petal members 1004 in a closed position around a doll 1006, representing a neonate, and two petal members 1004 in an open position. Similar to the examples of FIGS. 8 and 9, one petal member 1004 in the open position can receive the head of the neonate. Another petal member 1004 near the neonate's left leg, also in the open position, can provide visible or physical access to the neonate by a caregiver or a non-integral therapy component. Access to the neonate can be comforting to on-looking caregivers and parents by providing confirmation of therapy connections and monitoring of areas susceptible to wounds or chaffing. The neonate may be connected to multiple lines and tubes, traversing from a portion of the neonate to nearby machines or equipment. The access to the neonate by way of open petal members 1004 can provide the required entrance points without lifting, repositioning, or transferring the neonate from the care unit 1000. Similarly, the neonate can be placed into or lifted out of the care unit 1000 without having to disconnect therapy lines and tubes.

Optionally, one or more of the petal members 1004 can be configured to be detachable and attachable to a base member of the neonatal care unit 1000. Alternatively or additionally, one or more of the petal members 1004 can slide along a circumference or perimeter of the base member, as desired by the caregiver, or can include a folding configuration allowing the petal member 1004 to be stowed into a non-deployed position (e.g., within or tucked behind the base member) when not in use.

Optionally, a carrier, including a handle and one or more clips, can be included in the neonate care unit 1000. The one or more clips can mechanically couple the handle and the care unit 1000 to facilitate transfer of the care unit and an enveloped neonate from a first location to a second location spaced from the first location without altering the care unit's configuration. The carrier can provide a useful means when transferring neonates who are in a sleeping state.

Figure 11:
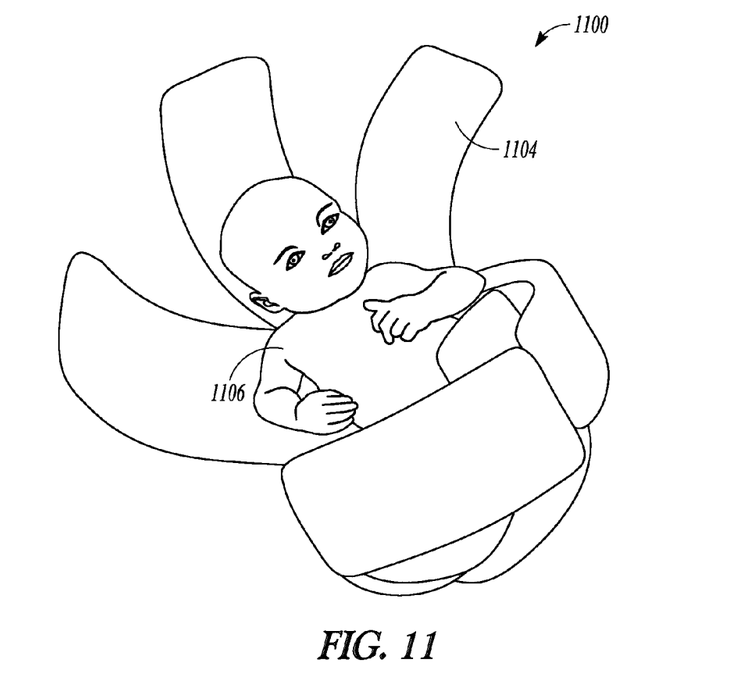
FIGS. 11 and 12 illustrate care units including a plurality of petal members in a closed position around a doll, representing a patient, and three petal members in an open position. One petal member is positioned to receive the head of the patient and the other petal members can provide visible access of the patient, such as for monitoring purposes.
Figure 12:
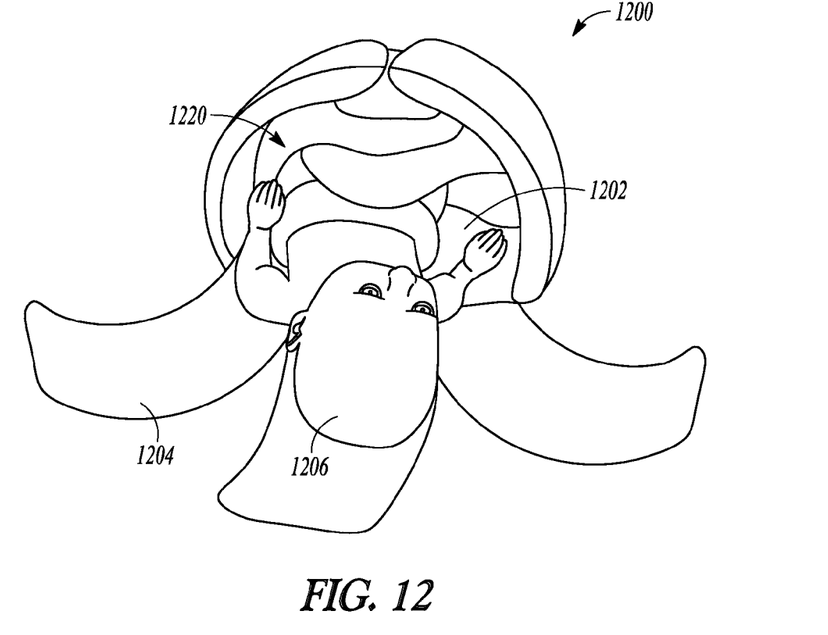

FIGS. 11 and 12 illustrate neonatal care units 1100, 1200 including a plurality of petal members 1104, 1204 in a closed position around a doll 1106, 1206, representing a neonate, and three petal members 1104, 1204 in an open position. Similar to the examples of FIGS. 8-10, one petal member 1104, 1204 in the open position can receive the head of neonate. The other petal members 1104, 1204 on each side of the pillow petal member 1104, 1204 can provide visible access to one or more portions of the neonate, such as for monitoring purposes.

As illustrated in FIG. 12, the neonatal care unit 1200, by way of a plurality of petal members 1204 and a base 1202, can define a cavity 1220 for receiving at least a portion of the neonate. The cavity can have a size and a shape that is customizable to a specific neonate for proper ventilation or chest expansion while breathing, for example. A cushioning material (not shown) can optionally fill the cavity 1220 to further secure or immobilize at least a portion of the neonate. In an example, the cushioning material can include a fluid- or gel-filled layer, which can provide elastic cushioning without introducing an electrocution hazard from therapy or sensor components and can optionally mimic a viscosity or other property of in vivo uterine amniotic fluid. In an example, the cushioning material can include memory foam or other porous material (e.g., sponge, beads, sand) that can conform to the neonate's shape. In an example, the cushioning material can include a conforming paper material strengthened with fibers or cables for structural integrity.

Figure 13:
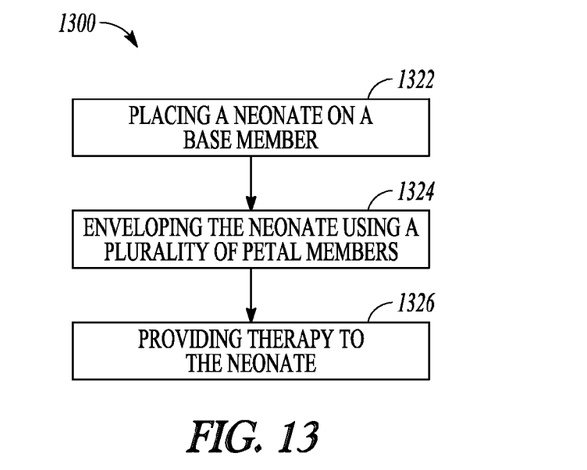
FIG. 13 illustrates a method of using a care unit, as constructed in accordance with at least one embodiment. The method can include placing a patient on a base member and wrapping a plurality of petal members around a portion of the patient.

FIG. 13 illustrates a method 1300 of using a neonatal care unit. At 1322, the method 1300 can include placing a neonate on a base member surrounded, at least in part, by a plurality of petal members. The petal members can have a first end engaged with the base member and a second end disposed longitudinally away from the base member. Placement of the neonate on the base member can include placing the neonate on a circular, oval, or octagonal base member surrounded by petal members around at least half of the base member's perimeter.

At 1324, the method 1300 can include enveloping the neonate by wrapping at least two of the plurality of petal members around a portion of the neonate and less than 360 degrees relative to respective petal member first ends. Petal members configured to secure the neonate without having to be wrapped 360 degrees or more, relative to respective first ends, eliminates the need for a caregiver to lift the neonatal care unit above a support surface as the petal members are wrapped. Stated differently, the segmented nature of the present petal members solves a burdensome problem of repeated lifting and placing of the neonate or the neonatal care unit in order to position a long ribbon of wrapping material. Using the present teachings, the neonate can be lifted and positioned a single time and the petal members can be positioned without additional lifting and positioning. Wrapping of the petal members around the neonate can include introducing a bend into one or more of the petal members, thereby providing support to the neonate's arms, hands, legs, feet, abdomen, or chest region and creating a customized cavity that allows for proper neonatal ventilation.

At least one petal member can maintain an open or partially open position to provide support to the neonate's head. Additionally or alternatively, at least one petal member can be disengaged from the base member to provide line or tube access between the neonate and a nearby machine. The disengaged petal member(s) can optionally be tethered to the base member using a string, coil, or other elastic member for easier engagement, when desired by a caregiver. The access to the neonate by way of disengaged petal member can provide an entrance without lifting, repositioning, or transferring the neonate from the care unit.

At 1326, the method 1300 can include providing therapy to the neonate. The therapy can include directing an optical light or a thermal energy wave toward a portion of the neonate. Diffusion or funneling of the optical light, for example, can be controlled using a diffusion film or other material inserted or attached near a light source. Optionally, the method 1300 can include monitoring the neonate using one or more sensor components.

The present neonatal care units satisfy outstanding needs by providing a comfortable environment for a neonate—full-term and preterm—that can simulate one or more features of a uterine environment, expedite or assist neonatal development, reduce a neonate's hospital stay, stress level, crying and severity of infections, and provide visual comfort to caregivers and parents unable to hold the neonate. The neonatal care units can maintain a desired neonatal positioning relative to a support surface on which the unit is placed to facilitate neuromuscular development. The present neonatal care units can provide optical, thermal or other therapy in close proximity to a neonate's skin (e.g., to benefit those that are jaundiced or hyperbilirubinemic), while restricting select neonatal movements and allowing for desired caregiver or equipment access to the neonate.

Optionally, the care units can be used for patients other than neonates, such as for geriatrics, pediatrics, adult care, and pet care applications.

The above Detailed Description includes references to the accompanying drawings, which form a part of the Detailed Description. The drawings show, by way of illustration, specific embodiments in which the present neonate care units and related methods can be practiced. These embodiments are also referred to herein as "examples."

The above Detailed Description is intended to be illustrative, and not restrictive. For example, the above-described examples (or one or more elements thereof) can be used in combination with each other. Other embodiments can be used, such as by one of ordinary skill in the art upon reviewing the above description. Also, various features or elements can be grouped together to streamline the disclosure. This should not be interpreted as intending that an unclaimed disclosed feature is essential to any claim. Rather, inventive subject matter can lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

In this document, the terms "a" or "an" are used to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated.

In the appended claims, the terms "including" and "in which" are used as the plain-English equivalents of the respective terms "comprising" and "wherein." Also, in the following claims, the terms "including" and "comprising" are open-ended, that is, an assembly, kit, or method that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The Abstract is provided to allow the reader to quickly ascertain the nature of the technical disclosure. It is submitted with the understanding that it will not be used to interpret or limit the scope or meaning of the claims.

What is claimed is:

1. A care unit comprising: a base member including a physical edge that defines a perimeter; and a plurality of petal members, each petal member extending from a first end, engaged with the base member at the perimeter, to a second end, spaced from the base member, the base member and the plurality of petal members having an inward-facing surface and an outward-facing surface, the plurality of petal members including at least a first petal member detachably connected to the physical edge and a second petal member, disposed on a second, different side of the base member, the first petal member and the second petal member positionable independently of one another, and the inward-facing surfaces of the base member and the first and second petal members are configured to define a cavity proximate a chest region of a patient when in a first position, the first and second petal members being configured to not rest on the chest region of the patient when the patient is positioned on his or her back and the first and second petal members at least partially surround the patient, wherein when in the first position, a first side of the first petal member and a second side of the second petal member define an opening configured to allow a caregiver access to at least a portion of the patient and equipment used for treatment or monitoring to pass into the cavity, wherein one or more of the plurality of petal members is manufactured from a material capable of maintaining a shape of the cavity solely due to a rigidity of the material and without use of a fastener member and the one or more of the plurality of petal members is configured to not rest on the chest region of the patient when the patient is positioned on his or her back and the first and second petal members at least partially surround the patient.

2. The care unit of claim 1, further comprising a therapy component, configured to provide a treatment to the patient, coupled to, or integrated with, one or both of the base member or one of the plurality of petal members.

3. The care unit of claim 2, wherein the therapy component includes one or more of an optical light source, a thermal energy source, an oxygen or air source, a sound wave source, a sound wave-cancelling source, or a pulsating source.

4. The care unit of claim 1, wherein the plurality of petal members are disposed around at least half of the perimeter of the base member.

5. The care unit of claim 1, wherein the base member defines a void configured to receive a flowable material to support the patient in a desired orientation.

6. The care unit of claim 1, wherein a size or a shape of the base member is adjustable.

7. The care unit of claim 1, wherein the base member includes an adjustment mechanism configured to maintain a selected angular alignment or a selected elevation between a plane of the base member and an underlying support surface on which the base member rests.

8. The care unit of claim 1, wherein at least one of the petal members includes a fastener member that, when in a loosened or detached configuration, permits the at least one of the petal members to change in shape or position and, when in a tightened or attached configuration, inhibits the petal member from changing shape or position.

9. The care unit of claim 1, wherein the outward-facing surface of each of the plurality of petal members have a hardness greater than each of the inward-facing surfaces.

10. The care unit of claim 1, wherein the outward-facing surface of at least one petal members includes indicia.

11. The care unit of claim 1, further comprising a sensor coupled to, or integrated with, one or both of the base member or one of the plurality of petal members for sensing or monitoring a condition of the patient.

12. The care unit of claim 1, wherein the first petal member detachably connected to the physical edge includes the first petal member configured to be detached and attached to the physical edge.

13. The care unit of claim 1, wherein each petal member and the base member include a contact-pressure monitor arranged and configured to generate a contoured map of pressure points for the patient.

14. The care unit of claim 1, further comprising at least one of the following: a rocking motion generator, a speaker for generating white noise, and an air filter unit to filter surrounding air.

15. A method comprising: placing a patient on a base member having a plurality of physical edges that define a perimeter, the base member surrounded, at least in part, by a plurality of petal members, each of the plurality of petal members having a first end detachably engaged with the base member at the perimeter and having a second end disposed longitudinally away from the base member; and enveloping the patient, including wrapping the plurality of petal members about a portion of the patient and less than 360 degrees relative to respective petal member first ends, wherein enveloping the patient includes wrapping the plurality of petal members in such a fashion that a cavity is formed proximate and above a chest region of the patient when the patient is positioned on his or her back, a first side and a second side of any two of the plurality of petal members define an opening configured to allow a caregiver access to the portion of the patient and equipment used for treatment or monitoring to pass into the cavity formed by the plurality of petal members, wherein wrapping the plurality of petal members about the portion of the patient includes introducing a bend into one or more of the petal members, wherein the plurality of petal members are manufactured from a material capable of maintaining a shape of the cavity solely due to a rigidity of the material and without use of a fastener member and the plurality of petal members are configured to not rest on the chest region of the patient when the patient is positioned on his or her back.

16. The method of claim 15, further comprising providing therapy to the patient.

17. The method of claim 16, wherein providing therapy to the patient includes directing an optical light or a thermal energy wave toward a portion of the patient.

18. The method of claim 15, wherein placing the patient on the base member includes placing the patient on a circular, oval, or octagonal base member surrounded by the plurality of petal members around at least half of the perimeter.

19. The method of claim 15, wherein wrapping the plurality of petal members about the portion of the patient includes providing support to the patient's arms, hands, legs, feet, abdomen, and chest region.

20. The method of claim 15, wherein wrapping the plurality of petal members about the portion of the patient includes creating a customized cavity that supports the patient and allows for proper ventilation.

21. The method of claim 15, further comprising maintaining a longitudinal extension, away from the base member, of at least one petal member, thereby providing support to the patient's head.

22. The method of claim 15, further comprising disengaging one or more petal members from at least one edge portion of the base member.

23. A care unit comprising: a base terminating at a physical edge that defines a perimeter of the base; a first petal detachably connected to a first portion of the perimeter; and a second petal detachably connected to a second portion of the perimeter, the second petal having a shape that is independently modifiable without disturbing the first petal, wherein, when in use, the first petal, the second petal, and the base is configured to define a cavity proximate above a chest region of a patient when the patient is positioned on his or her back, the first petal and the second petal defining at least one opening configured to allow a caregiver access to at least a portion of the patient and equipment used for treatment or monitoring to pass into the cavity, wherein each petal includes an impact resistant material capable of maintaining an autonomous shape independent of the other petal solely due to a rigidity of the material and without use of a fastener member and each petal is configured to not rest on the chest region of the patient when the patient is positioned on his or her back and the first and second petals at least partially surround the patient.

* * * * *